United States Patent [19]
Gazzara et al.

[11] Patent Number: 5,246,010
[45] Date of Patent: Sep. 21, 1993

[54] METHOD AND APPARATUS FOR EXHALATION ANALYSIS

[75] Inventors: Peter Gazzara, Reading; John Burke, Melrose, both of Mass.

[73] Assignee: Biotrine Corporation, Woburn, Mass.

[21] Appl. No.: 770,542

[22] Filed: Oct. 3, 1991

Related U.S. Application Data

[63] Continuation-in-part of Ser. No. 625,907, Dec. 11, 1990, abandoned.

[51] Int. Cl.$^5$ .............................................. A61B 5/087
[52] U.S. Cl. ...................................... 128/725; 482/13
[58] Field of Search ................. 128/725, 727, 729; 73/861.71, 861.74; 482/13

[56] References Cited

U.S. PATENT DOCUMENTS

| | | | |
|---|---|---|---|
| 254,443 | 3/1880 | Adams | D24/17 |
| 471,389 | 3/1892 | Lacey . | |
| 1,541,750 | 6/1925 | Park . | |
| 3,298,362 | 1/1967 | Lippitt, Jr. et al. | 128/2.05 |
| 3,635,214 | 1/1972 | Rand et al. | 128/2.08 |
| 3,720,202 | 3/1973 | Cleary | 128/2.08 |
| 3,797,479 | 3/1974 | Graham | 128/2.08 |
| 3,826,247 | 7/1974 | Ruskin et al. | 128/2.08 |
| 3,958,565 | 5/1976 | Wright | 128/2.08 |
| 4,041,935 | 8/1977 | Garbe | 128/2.08 |
| 4,210,155 | 7/1980 | Grimes | 128/727 |
| 4,768,520 | 9/1988 | Varraux et al. | 128/725 |
| 4,944,306 | 7/1990 | Alvino | 128/725 |
| 5,067,707 | 11/1991 | Kohnke | 128/725 |

OTHER PUBLICATIONS

Peak Performance—A strategy for Asthma Self-Assessment, by Guillermo R. Mendoza, M.D.

Primary Examiner—Lee S. Cohen
Assistant Examiner—Brian L. Casler
Attorney, Agent, or Firm—Fitch, Even, Tabin & Flannery

[57] ABSTRACT

The present invention is a method for determining human expiratory flow rate, comprising a peak flow meter and a zone calculator. The peak flow meter is used to determine what the user's peak expiratory flow rate is in conjunction with medical data compiled on the zone calculator. The individual's peak expiratory flow rate and predetermined sub-optimal values are applied to the peak flow meter as color zone settings. The peak flow meter thus set is ready for the individual to use to determine whether he is functioning in the peak expiratory flow rate color zone, or one of the sub-optimal expiratory flow rate color zones. The color zones correspond to specific remedial measures to be followed by the individual in case of sub-optimal expiratory flow rate.

12 Claims, 6 Drawing Sheets

METHOD AND APPARATUS FOR EXHALATION ANALYSIS

CROSS-REFERENCE TO RELATED APPLICATIONS

This is a continuation-in-part of co-pending U.S. patent application Ser. No. 625,907 entitled "Method and Apparatus For Exhalation Analysis," filed on Dec. 11, 1990 now abandon.

FIELD OF THE INVENTION

The present invention is directed to a method and an apparatus for determining human peak expiratory flow rate. More particularly, the present invention is directed to a method and an apparatus which indicate whether an asthmatic is functioning at his optimal lung exhalation flow rate, or deviations therefrom, and the indication therefrom may be used to initiate remedial actions which have been recommended for the asthmatic.

BACKGROUND OF THE INVENTION

This invention relates to a method and an apparatus for determining human peak expiratory flow rate, to indicate to the asthmatic what course of action to pursue or what regimen of medication to follow, relative to the asthmatic's present ventilatory state.

This invention is designed for asthmatics, because these individuals have a need for determining their current lung exhalation flow rates and deviations from their own optimal or peak flow rate. This determination can help asthmatics decide or follow previously recommended remedial actions they need to take.

The onset of asthmatic symptoms may occur quickly or slowly. The faulty subjective assessment of an asthmatic's own condition by the patient can result in lack of detection of early obstruction of air passageways. If early obstruction, an early warning signal, is not detected, the patient will not exercise measures which stem worsening of the asthmatic episode. It is to the benefit of those with severe asthma, and those with mild obstruction to air passage, to be able to detect early warning signals. Those with severe asthma may have trouble relying on the more obvious warning signals which become evident too late, since an asthmatic episode may result in rapid deterioration of air exhalation flow rate. Those with mild obstruction to air passage, too, would benefit by the knowledge that they are not performing at their peak expiratory flow rate. Thus, it is important that asthmatics be able to quantify quickly and accurately the deviations from their normal peak lung flow rate in order to take appropriate remedial actions.

This invention can overcome some of the limitations which exist in the art today. An asthmatic may have somewhat narrowed airway passages which may not be detected by a physician using a stethoscope. In contrast, this invention allows detection of even subtle changes in air flow rate, giving the individual more information as to current state. With this system, a more refined approach is used in asthma management, where very moderate changes in the asthmatic's state may be countered with moderate adjustments in remedial actions.

The instrument allows the individual to take the guesswork out of self-management. The individual may check for reduced airway flow rate before bedtime, and ward off the possibility of an attack in the middle of the night. Thus, this system permits severe attacks to be warded off by allowing detection of the early warning signal, low-grade air passage obstruction. There are other "metering" devices on the market which indicate the peak lung exhalation flow of a human, yet these devices are not part of a system which quantifies the deviation from optimal peak expiratory flow in an easy and accurate manner. Use of this system yields information of lung flow rate deviation for which the user may take the appropriate remedial measures.

The system effectively acts as a biofeedback device. With it, the asthmatic learns to recognize subtle symptoms. In the long run, the asthmatic will become knowledgeable as to his or her own physiological state. Thus, the asthmatic will have learned the subtle signs that indicate mildly reduced peak expiratory flow rate, and will be able to undertake remedial actions to reduce the chance of further airflow reduction. Thus, the system helps achieve an asthmatic's long term goal of self-vigilance and accurate perception of one's state.

Today's asthmatic and in particular children may be active individuals. The devices which make up this system are very compatible with that lifestyle. In this regard, the peak flow meter itself is small, lightweight, portable, and reusable. Also, it is preferably constructed so that children may use or play with it without damaging it or resetting indicators on it. That is, the indicators used to indicate the necessity of remedial action based on the asthmatic's current expiratory flow rate should be set by a physician and should not move from the position set by the physician, despite rugged transport or handling of the device. The device is characterized by simplicity and economy of manufacture. A sleeved card which contains the compiled data is a lightweight, flat device of dimensions 4"×8" or less. This may be contrasted with another airflow metering device available which has a vertical tower which serves as the meter, attached to a horizontal cylindrical section into which the user blows. Such an instrument would not be as convenient as the present invention for the individual to carry.

From the foregoing, it will be seen that a need has arisen for a system which integrates use of an airflow metering device into an asthmatic's active life. Need is felt for a system which detects subtle and gross changes in the asthmatic's peak expiratory flow rate, so that even a mild reduction of such flow rate is promptly dealt with in a systematic fashion. The present invention is aimed at providing such a system.

A general object of the invention is to provide an improved peak flow metering device for use by asthmatic individuals.

Another object of the invention is to provide a system to evaluate the current status of an individual with respect to peak expiratory flow rate and deviations therefrom.

These and other objects will become more apparent from the following detailed description and the appended claims.

SUMMARY OF THE INVENTION

In accordance with the present invention, the asthmatic is provided with the ability to utilize color zones indicating optimal expiratory flow rate and deviations therefrom when using a peak flow meter. The preferred flow meter has a plurality of zones and settable indicators which define the zones. The setting of the indicators is preferably done by a physician (although it could be done by a patient) who uses a personal zone calculator on which are compiled patient data relative to peak expiratory flow rate for persons of given characteristics such as age and size and gender. The normal or peak expiratory flow rate for a particular individual is determined by the individual blowing into the peak flow meter multiple times, resetting the moveable indicator between puffs. This information, in conjunction with the predicted peak value revealed on the personal zone calculator, determines what the individual's optimal lung exhalation flow rate is. The asthmatic's optimal value thus determined is set usually by the physician in his office, on the personal zone calculator to reveal values of a predetermined quantity below the optimal value, e.g. 10% or 50% below the optimal value. This data is then applied, usually by the physician, to the peak flow meter, preferably by the physician sliding the color-coded indicators along a scale to define the three different color zones. When the color-coded indicators are set on the peak flow meter, it has been individually adjusted for the asthmatic to use to determine peak expiratory flow rate. In one embodiment, the present device provides high friction color-coded indicators so that after being set by a physician, the indicators do not vary from their set position. This prevents the indicators from sliding during transport or rough handling particularly by children, which would result in a faulty comparison of the asthmatic's present condition to optimal conditions.

Subsequent to setting the peak flow meter in this way, the asthmatic uses it to determine peak expiratory flow rate. To this end, the asthmatic blows into it and reads in which zone the moveable indicator has come to rest. If the moveable indicator comes to rest in a zone which indicates deviation from optimal expiratory flow rate, the asthmatic uses the color zone indication to determine what remedial actions to take. The physician will have instructed the asthmatic on appropriate remedial actions to take. If the moveable indicator comes to rest in the zone which indicates that optimal expiratory flow rate exists, then the user need not take remedial measures.

BRIEF DESCRIPTION OF THE DRAWINGS

The present invention will be described in connection with the accompanying drawings, which illustrate the preferred embodiments of the invention, and in which.

DETAILED DESCRIPTION OF THE INVENTION

Figures 1, 2, 3, 4, 5, 6:
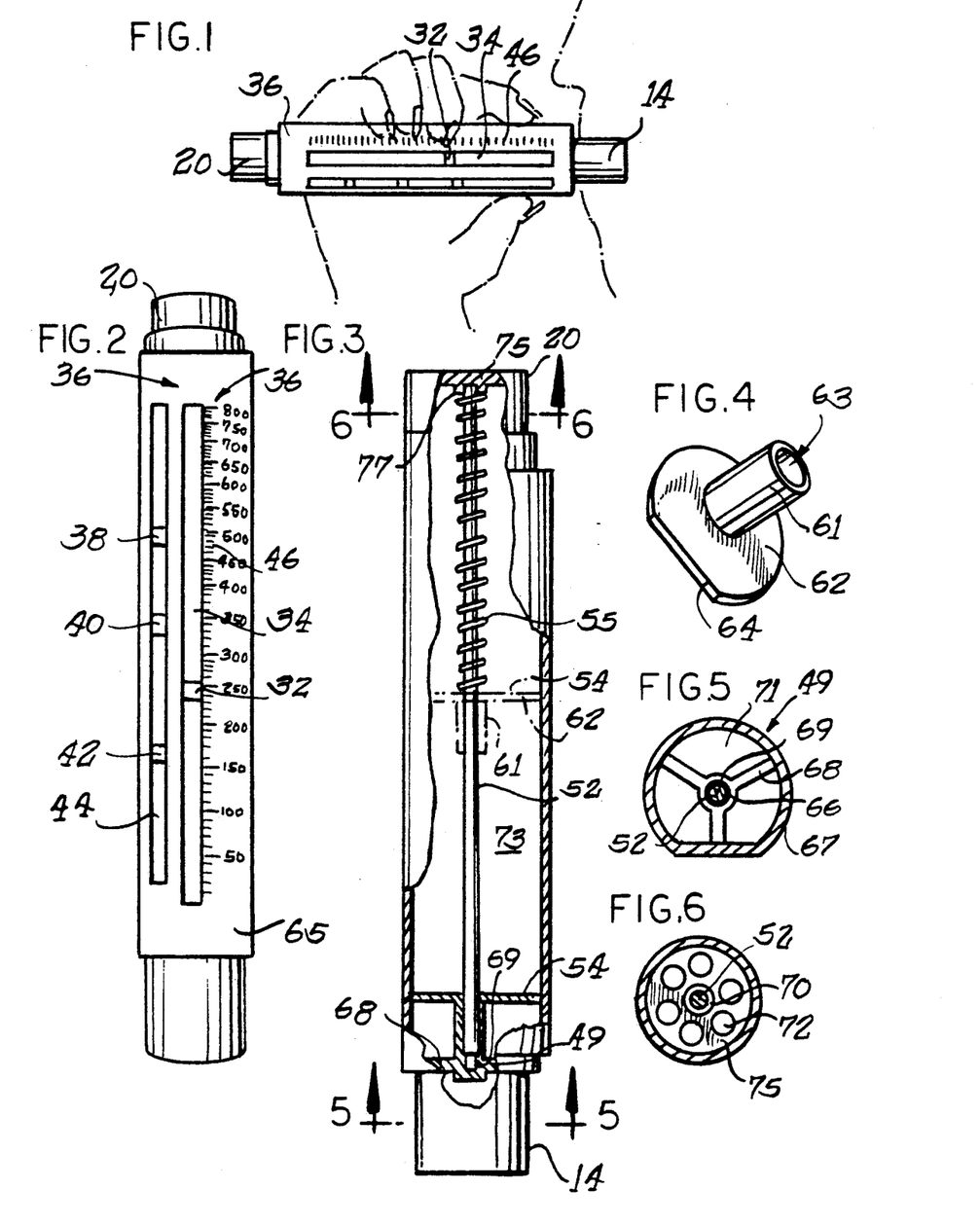
FIG. 1 is a front elevational view of a peak flow meter in accordance with the invention.
FIG. 2 is an enlarged elevational view of the peak flow meter, illustrating the scale and accompanying indicators.
FIG. 3 is an elevational view of the peak flow meter, partially broken away.
FIG. 4 is a perspective view of a piston used in accordance with the invention.
FIG. 5 is a cross-sectional view of the peak flow meter taken along the line 5—5 of FIG. 3.
FIG. 6 is a cross-sectional view taken along the line 6—6 in FIG. 3.

Now, referring to the drawings, a first embodiment of the peak flow meter of the invention is generally shown in FIG. 1. In this embodiment, the peak flow meter is a lightweight instrument having a body 36 of which can be held in the hand while an air inlet 14 is placed in the mouth of the user. The body 36 is preferably formed of aluminum, such as by extrusion, to provide a rugged and durable device. A moveable indicator 32 slides along a slit 34 in response to the user blowing air in through the air inlet 14 and air exhausts through the body at an air outlet 20. Once an individual knows his optimal expiratory flow rate, the individual can evaluate whether he is functioning at optimal expiratory flow rate by using the peak flow meter.

The present invention provides the asthmatic with information regarding subtle and gross changes in his peak expiratory flow rate. The present invention comprises a method for determining flow rate for air exhalation by the lungs using a peak flow meter 36. An individual's peak expiratory flow rate is determined. Using that information, predicted expiratory values are determined and applied in the form of zone settings defined by zone indicators 38, 40 and 42 on the peak flow meter. A zone calculator may also be provided to the asthmatic to set his own zones but it is preferred that the physician and not the patient be given the personal zone calculator 36. Alternatively, the physician may consult his own tables or charts to define the zones. The peak flow meter is then ready for use. The individual concerned about his current expiratory flow rate may blow into the peak flow meter and read what his current color zone is. The color zone indicates to the asthmatic individual whether remedial action need be taken. Preferably, the zones are color-coded although they need not be color-coded. For example, the zones could be coded numerically as zones 1, 2 and 3; or alphabetically as zones A, B and C; or by words such as "peak", "ten percent" and "fifty percent". The number of zones and their extent may also be varied from that described herein.

Figures 7, 8:
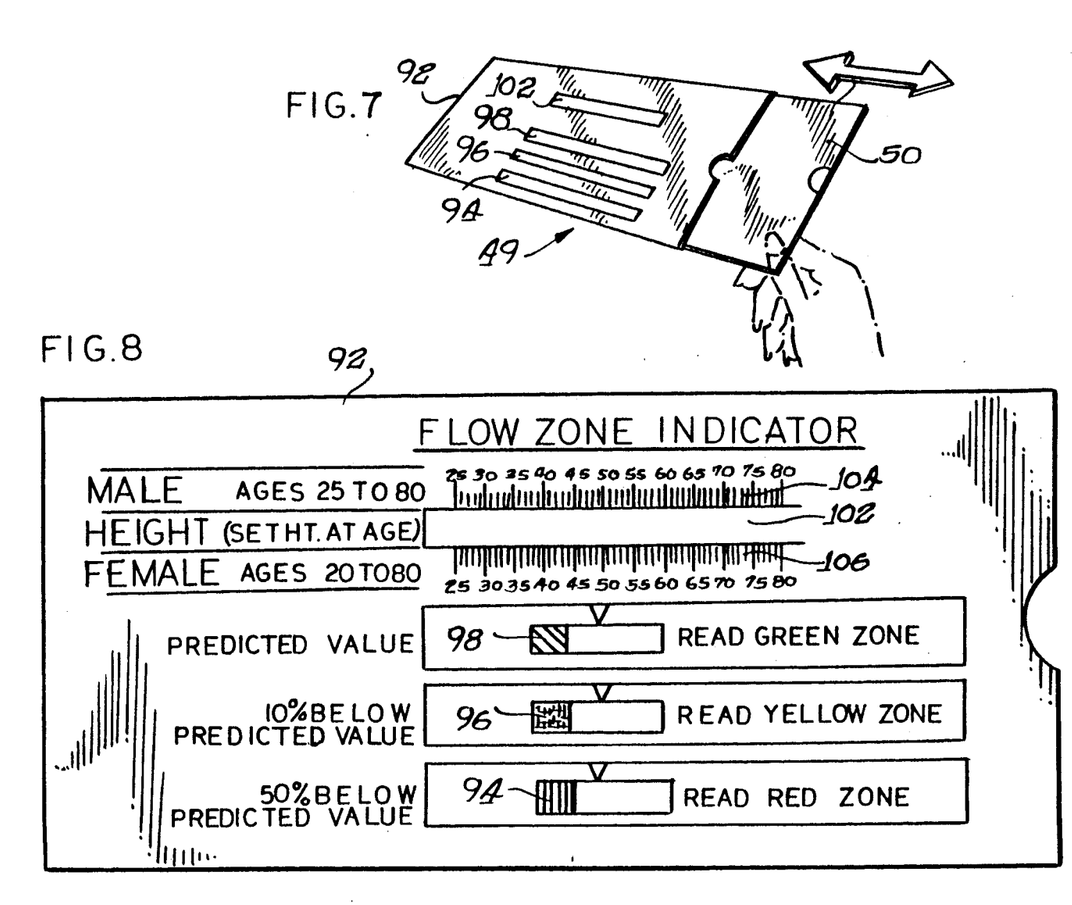
FIG. 7 is a perspective view of a zone calculator in accordance with the invention.
FIG. 8 is an enlarged elevational view of a sleeve of the zone calculator in accordance with the invention.

Turning now in greater detail to the first embodiment illustrated in FIG. 2, it will be seen that this figure is a more detailed representation of the peak flow meter shown in FIG. 1. The body 36 of the peak flow meter in FIG. 2 is visible, as are the elements on the face side of the apparatus. Most obvious is non-linear scale 46 oriented alongside the slit 34. The air outlet through which air exhausts is visible at 20. The moveable indicator 32 moves in the slit 34. Three color zone indicators 38, 40, and 42 move in a track 44. The color zone indicators 38, 40, and 42 are set at the positions along the scale 46 that correspond to the values preferably obtained by using the compiled data on a personal zone calculator which is represented in FIG. 7. Alternatively, a physician may consult other texts and data to set the zones. The mounting of the indicator 32 and the color zone indicators 38, 40 and 42 for sliding movement is described further below in connection with the alternative embodiment of the invention. The indicator which corresponds to the peak expiratory flow rate 38 is green. The indicator which corresponds to 10% below the peak expiratory flow rate 40 is yellow. The indicator which corresponds to 50% below the peak expiratory flow rate 42 is red. Other colors may be used. The preferred zone calculator is in the form of a slide chart or slide rule but manifestly the calculations made could be done using an electronic computer chip or calculator.

As represented by FIG. 2, the peak flow meter 36 is used in cooperation with the personal zone calculator 49 which is represented by FIG. 7. Focusing on FIG. 2, the settings for the three color zone indicators 38, 40, 42 are obtained by reading the personal zone calculator 49 (FIG. 7) and are moved in the track 44 to the appropriate settings. Before using the peak flow meter to identify diminished expiratory flow rate, the user must determine what is his optimal expiratory flow rate. To do this, the moveable indicator 32 (FIG. 2) is set at the lowest point in the slit, corresponding to zero on the non-linear scale 46. The user then places the air inlet 14 to his lips and blows air into the peak flow meter. The air blown through the body of the peak flow meter 36 pushes the moveable indicator 32 along the slit 34 to a position where it comes to rest and stops there. The position of the indicator on the non-linear scale 46 which is oriented alongside the slit 34 can be read. The user observes the value on the scale at which the indicator comes to rest, and repeats the process two times. The highest of these values indicates to the physician the user's individual peak expiratory flow rate.

The physician or the user then consults the personal zone calculator 49 (FIG. 7) to compare the user's individual peak expiratory flow rate with the average predicted value based on age, height, and sex which is presented in the compiled medical research presented on the personal zone calculator 49. A card 50 is slid through a sleeve 92. On the card 50 are compiled medical research which are visible through windows 94, 96, 98 in the sleeve 92. As the card 50 is slid through the sleeve 92, different data are revealed through the windows 94, 96, 98. A more detailed depiction of the sleeve 92 of the personal zone calculator is shown in FIG. 8. It can be seen that on the sleeve 92 adjacent to the windows are printed indicators for the windows. Alongside a window 102 are scales of age in years for both males 104 and females 106. Visible through the window 102 are varying heights of individuals. To use the personal zone calculator, the asthmatic slides the card through the sleeve until his height, visible on the card through window 102 lines up with the correct age on the scale 104 (in this case, for males). Once this is done, the values corresponding to the predicted expiratory flow rate and the deviations from predicted lung expiratory flow rate are visible through the windows 94, 96, 98. Adjacent to each of the windows 94, 96, 98 is indicated one of the color zones. The color green is adjacent to window 98 and yellow is adjacent to window 96. Adjacent to window 94 is the corresponding color red. Adjacent to the windows 94, 96, 98 are arrows which point into the windows. The value beneath the arrow that is visible through window 98 corresponds to the predicted value of expiratory flow rate for individuals of that age, height, and sex. Similarly, the value beneath the arrow visible through window 96 corresponds to another value, for example, 10% below the predicted value as indicated on the sleeve. In a similar fashion, the value beneath the arrow visible through window 94 corresponds to a still further value, for example, 50% below the predicted value of peak expiratory flow rate for individuals of that age, height, and sex. These first and second values of 10% and 50% are merely exemplary, and the physician may deviate therefrom.

The physician or user compares the highest value achieved by blowing into the peak flow meter with the value that is the predicted peak expiratory flow rate for individuals of that age, height and sex. If the highest number achieved by blowing into the peak flow meter is much less than the physician's desired flow rate, the physician may prescribe further remedial actions. If the highest number achieved by blowing into the peak flow meter is visible in the window 98, or is higher than the values visible in the window, then this value is the individual's optimal expiratory flow rate. Once the individual's optimal expiratory flow rate is determined, the physician will set the personal zone calculator so that the user's optimal value is set beneath the arrow in window 98 so that the individual's sub-optimal lung capacities can be read through windows 94 and 96. At this point all three values may be applied to the peak flow meter (FIG. 2) by sliding the colored indicators 38, 40, 42 along the track 44 to the appropriate values on the non-linear scale 46. The optimal peak expiratory flow rate is set on the green indicator 38. A first value, for example, 10% below optimal expiratory flow rate, is set on the yellow indicator 40. A second value, for example, 50% below optimal expiratory flow rate, is set on the red indicator 42. High friction between the colored indicators and the body of the apparatus prevents the colored indicators from inadvertently sliding from the position set by a physician.

For this asthmatic, the physician has now set individualized values on the peak flow meter. The meter is ready to be used by that individual to detect possible reduction in airflow. To do this, the asthmatic checks to be sure that the colored indicators (FIG. 2) 38, 40, 42 are in the proper positions along the scale 46. In this regard, the settings of the colored indicators as established by the physician using the personal zone calculator are recorded in a log for the patient to retain so that should the colored indicators move from their set position, the patient can then reset the indicator to its proper position. For instance, if a child moves the colored indicators, his parent can reset the indicators by consulting the log.

The user then blows as hard as he can into the peak flow meter and reads the color zone that corresponds to his present expiratory flow rate. If the moveable indicator 32 comes to rest higher on the scale than the green indicator or between the green indicator 38 and the yellow indicator 40, then the user is said to have optimal expiratory flow rate, and is in the green zone. If the moveable indicator 32 comes to rest at the yellow indicator 40 or between the yellow indicator 40 and the red indicator 42, then the user is said to have 10% below optimal expiratory flow rate, and is in the yellow zone. If the moveable indicator 32 comes to rest at or below the red indicator 42 then the user has 50% below optimal expiratory flow rate, and is in the red zone. With such information, the user can take remedial actions if his expiratory flow rate is in the yellow or red zones. The physician will have explained to the user, and/or to his parent, if the user is a child, the appropriate remedial measures to take.

Turning in more detail to the functioning of the peak flow meter, FIG. 3 is a depiction of the peak flow meter of the first embodiment which is partially The air inlet 14 is visible, as is the end 20 through which air exhausts. A disc which corresponds to the air inlet 14 is shown in cross-section at 49. FIG. 5 also represents the air inlet disc 49. FIG. 5 is an end-on view of the disc which is shown in cross-section in FIG. 3 at 49. An end means through which air exhausts 75, FIG. 3, is also seen in an end-on view in FIG. 6. Visible in FIG. 3 is a centrally located, axially extending slide bar 52. This bar extends the length of the peak flow meter, attaching at either end to the end discs represented by 49 and 75. This bar supports a piston 54 which travels along the bar. Air blown in through the air inlet 14 pushes the piston to slide along the slide bar as indicated by the hatched piston 54. The piston 54 pushes to compress a constant rate spring 55 which resists the piston 54 travel and expands to return the piston once the air pressure of exhalation ceases. The spring 55 is shown only diagrammatically in FIG. 3. A spring arrangement is described in greater detail for the embodiment of FIGS. 11-18 in which the spring is a coiled tension spring which is elongated under the influence of the piston 54, as will be described further below. The piston 54 pushes against the moveable indicator 32. When airflow ceases, the piston 54 returns to the starting point, leaving the indicator at the maximal point of airflow. The piston merely abuts the indicator 32 when the indicator 32 is manually slid to its initial starting point against the piston. The piston separates from the indicator 32 when its returned by the spring. This indicates the individual's current peak expiratory flow rate, which is readable on the scale 46, and the individual's current expiratory flow rate is determined by reading in which color zone the indicator stopped. The scale 46 is non-linear and the constant rate spring accommodates use of a single instrument by both adults and children.

The piston 54 is shown in more detail in FIG. 4. It consists of a cylindrical portion 61 having a bore 63 through which the axial slide bar extends, and a flat disc-like portion 62 which blocks the flow of air and is pushed along by the air when the user exhales into the peak flow meter. The spring is connected to the disc 62. The shape of the disc-like portion is made to fit within the hollow cylinder of the peak flow meter, in the preferred embodiment it has a flattened edge 64 to slide along the flat front face portion 65 (FIG. 2) of the body 36. Alternatively, the shape of the disc-like portion 62 could be round to fit within a round body of the peak flow meter. Another embodiment of the disc-like portion would be square fitting within a square body of the peak flow meter. The purpose of the disc is to allow the piston to respond to the forced air as the asthmatic blows into the peak flow meter.

FIG. 5 is a cross-sectional view of the air inlet. It can be seen in the preferred embodiment that the air inlet 49 comprises a molded, plastic cylindrical wall 67 having three radially, inwardly extending arms 68 which support a small central hub 66. The hub 66 has an inwardly facing seat 69 (FIG. 5) to receive and support one end of the slide bar 52. Between the support arms are three sector shaped passages 71 through which air flows from the inlet into a hollow tubular chamber 73 in the body 36 of the peak flow meter.

The other end of the peak flow meter body supports the slide bar 52 and is vented to permit air exhaust from the body chamber 73. Herein, the venting is achieved through a series of vent openings 72 of circular shape in a molded end wall 75. The end wall has a central seat hub 77 into which is seated an end of the slide bar 52.

Both of the end discs 49 and 75 are integral with the body 36 of the peak flow meter, remaining attached thereto throughout usage. To wash the apparatus, the entire peak flow meter apparatus is simply inserted into a dishwasher or washed manually, and there is no need to remove the end discs 49 and 75 to thoroughly wash the apparatus. Furthermore, not only are the end discs 49 and 75 not separable from the remainder of the apparatus, but no other parts are separable either. Thus, the apparatus can be safely used by children without concern the small parts will be swallowed.

Figure 9:
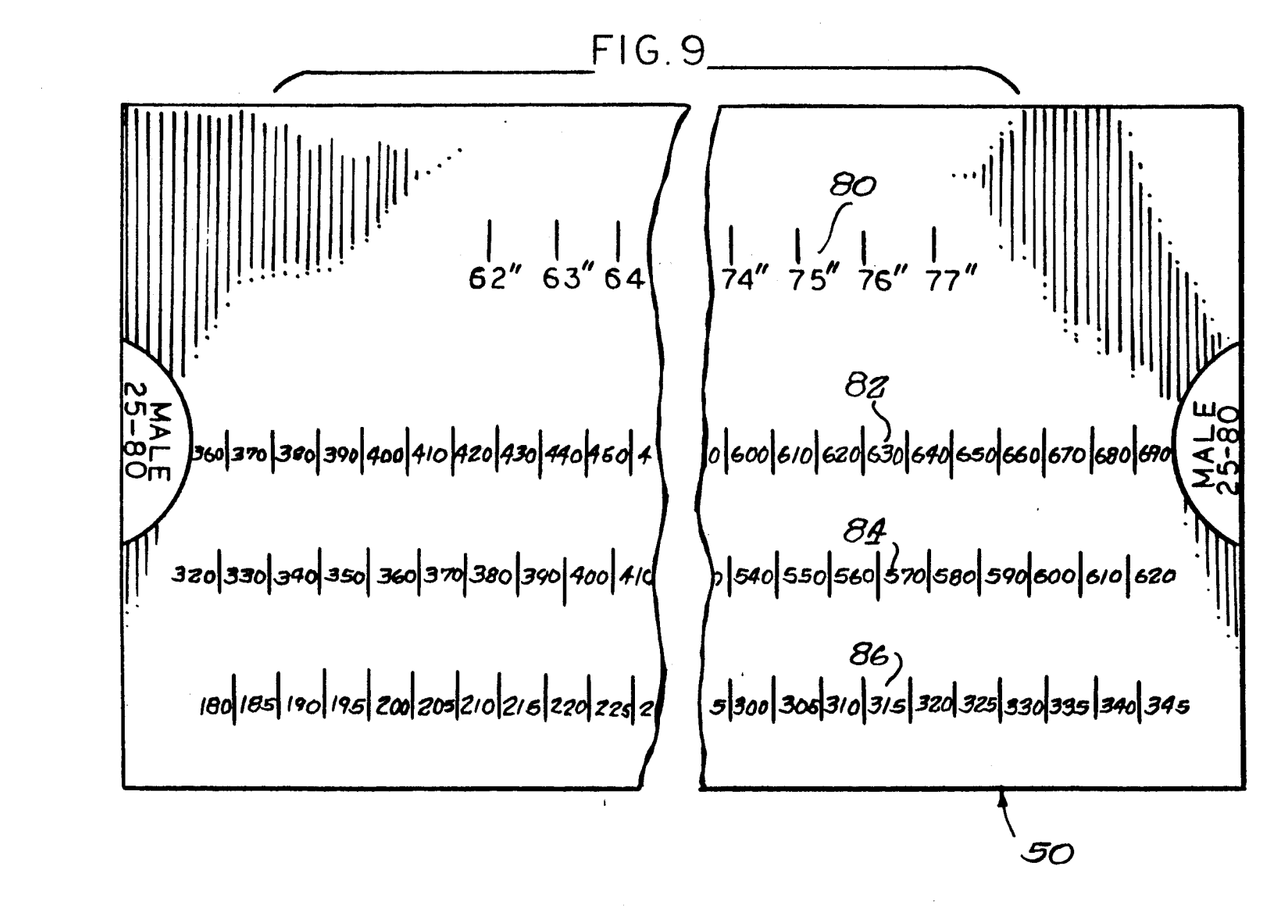
FIG. 9 is a broken, elevational view of a card of compiled data of the zone calculator.
Figure 10:
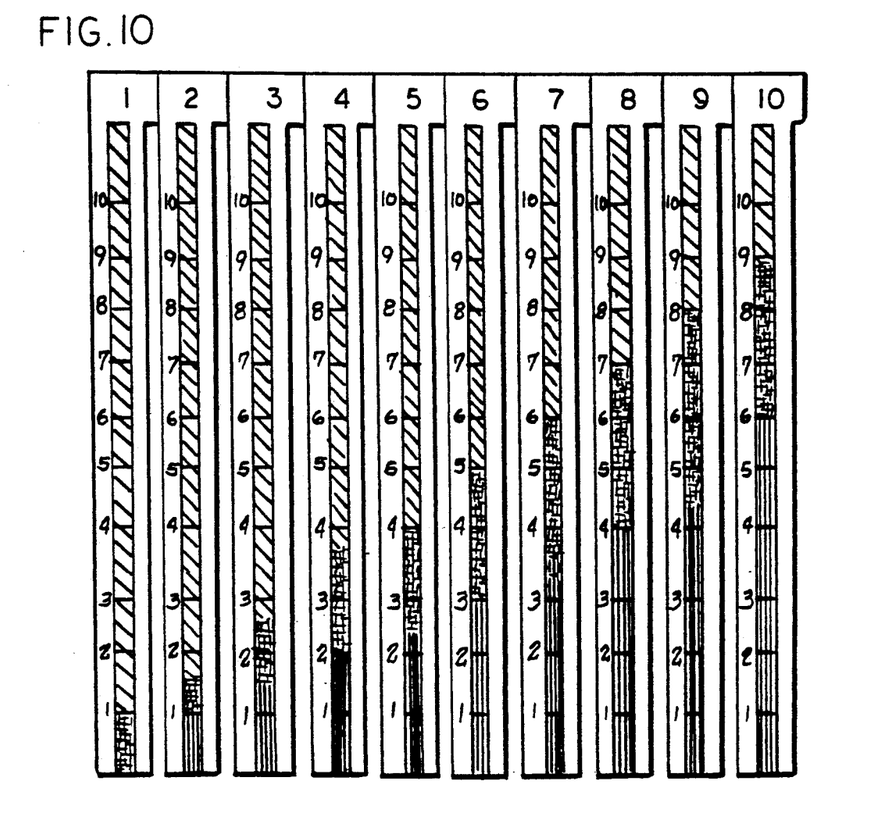
FIG. 10 is a series of plots, depicting the peak flow performance system.
Figure 11:
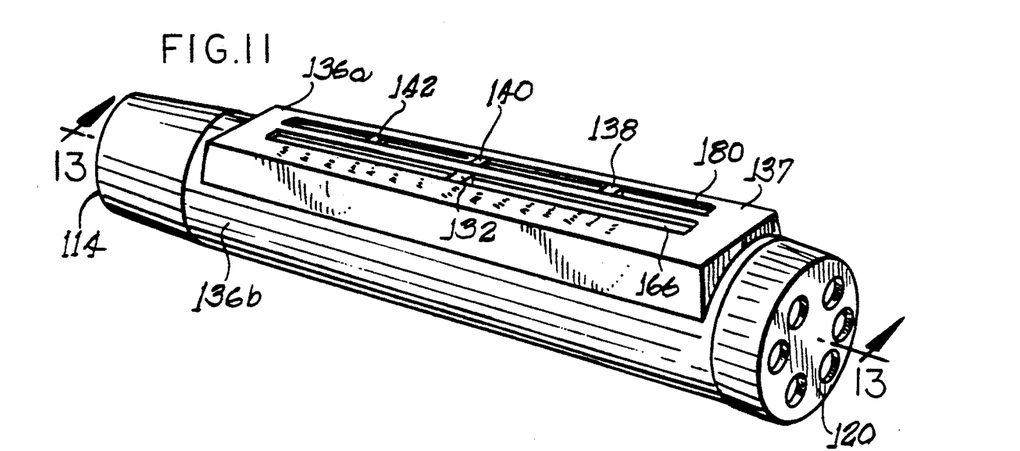
FIG. 11 is a perspective view of a second embodiment of a peak flow meter embodying various features of the present invention.
Figure 12:
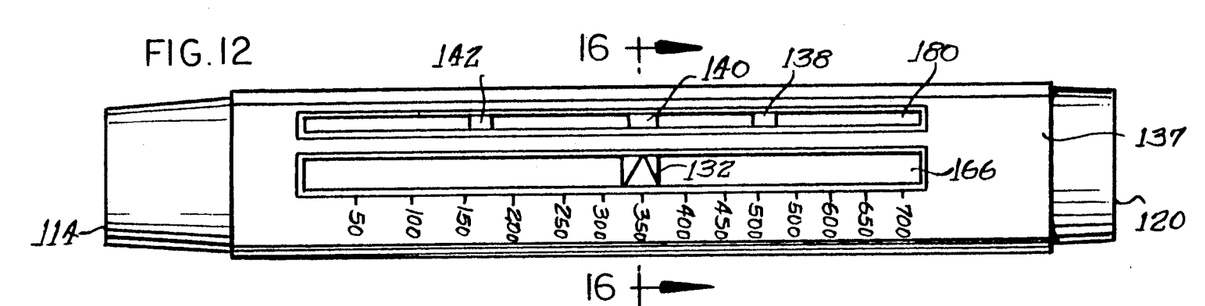
FIG. 12 is a plan view of the peak flow meter of FIG. 11.

Turning to the preferred embodiment of the personal zone calculator (FIG. 7), it can be seen that there are two moveable means to this portion of the invention. The card 50 is sized to closely fit and to slip inside the sleeve 92. In the preferred embodiment of the card FIG. 9, there is a row of data corresponding to individual person's heights 80, and rows of medical data relating to predicted expiratory flow rates for individuals of a particular category 82, 84, 86. The numbers are oriented increasing from left to right.

A more detailed view of the sleeve 92 is shown in FIG. 8. The preferred embodiment of the sleeve was described above in reference to the functioning of the personal zone calculator in cooperation with the peak flow meter. The sleeve has four rectangular windows (FIG. 8) 94, 96, 98, 102. Adjacent to window 102 are aligned scales of age in years for both males 104 and females 106. Visible through window 102 is a scale of individual's heights. The user lines his height up under his age on scale 104, and reveals in the windows below, 94, 96, 98 the average values of expiratory flow rate and deviations therefrom. Window 98 is the green window, and the value which is revealed through that window by the arrow pointing into the window is the predicted value of expiratory flow rate for an individual of a certain age, sex and height. Window 96 is the yellow window, and the value which is revealed by the arrow which points into that window is 10% below the predicted expiratory flow rate for such an individual. Window 94 is the red window and the value which is revealed by the arrow which points into that window is 50% below the predicted expiratory flow rate for such an individual.

The preferred embodiment of the personal zone calculator is that illustrated in FIGS. 7 and 8, but it has other forms. Another form of this part of the invention would be a wheel form, in which windows on a disc reveal compiled medical data presented on another disc which is visible through the windows. Such discs could be spun in relation to one another, so that different data are revealed in different orientations.

Figures 13, 14:
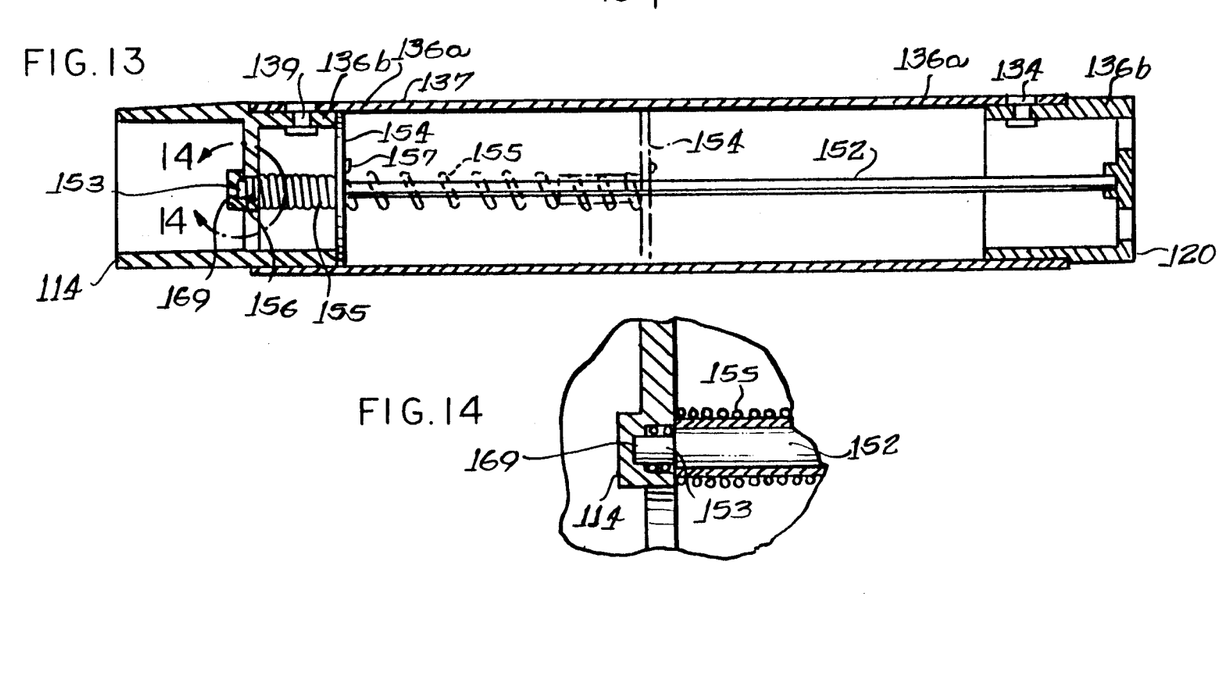
FIG. 13 is a cross-sectional view of the peak flow meter of FIG. 11 taken along line 13—13 of FIG. 11.
FIG. 14 is an enlarged, partial cross-sectional view of the spring mechanism of the peak flow meter of FIG. 11, taken along line 14—14 of FIG. 13.

Another embodiment of the peak flow meter of the present invention is illustrated in FIGS. 11-18. The peak flow meter includes a body 136 comprised of a generally cylindrical, piston housing portion 136b and an indicator housing portion 136a which is securely attached to the piston housing portion 136b by rivets 139, as best seen in FIG. 13. The rugged construction includes a sturdy aluminum body 136 and indicators that can be put into a dishwasher for cleaning and which will withstand abuse by a child.

With further reference to the cross-sectional view of FIG. 13, the peak flow meter of this embodiment employs a tension spring 155 in contrast with the compression spring 55 seen in FIG. 3. That is, in this embodiment, the spring 155 is extended as the piston 154 advances in response to breath exhalation, rather than being compressed as in the embodiment of FIGS. 1-6.

Figure 15:
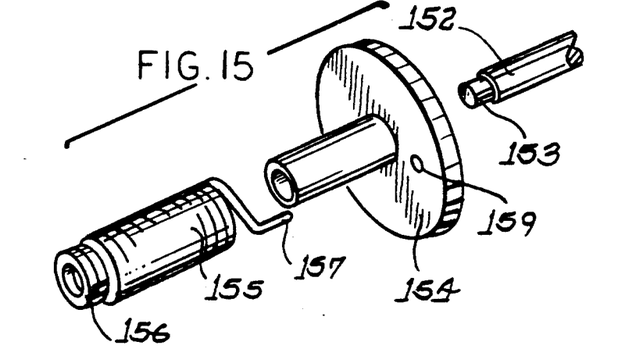
FIG. 15 is an enlarged perspective view of the spring and disc arrangement of the peak flow meter of FIG. 11.

The arrangement of the spring mechanism of this embodiment is further illustrated in FIGS. 14 and 15. As with the previous embodiment, the slide bar 152 extends from the inlet end 114 to the outlet end 120 of the flow meter and includes a reduced end 153 which is received in inwardly facing seat 169, and opposite reduced end 151 which is received in central seat hub 177. The piston 154 is slidable on the slide bar 152 and moves in response to, and in proportion to, the force of breath exhalation. The spring 155 is a coil spring which includes a mounting end 156 of reduced diameter, which end 156 is received and secured in the inwardly facing seat 169. The opposite end of the spring 155 includes an extending portion 157 which is fixedly secured within aperture 159 of the piston 154.

Thus, when a user exhales into the inlet 114 of the apparatus, the piston 154 is pushed away from the user and the spring 155 is extended as illustrated in phantom in FIG. 13.

The piston merely abuts the indicator 132 when the indicator is at its starting position and separates from the indicator when the piston is being pulled in the return direction by the spring 155. Subsequently, at the termination of exhalation, the spring returns to its contracted position indicated by solid lines in FIG. 13.

Figure 16:
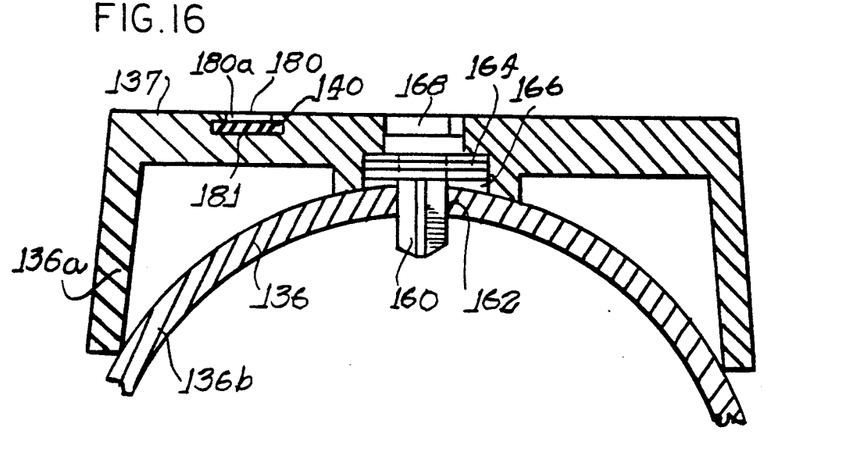
FIG. 16 is an enlarged cross-sectional view of the peak flow meter of FIG. 11 taken along line 16—16 of FIG. 12.
Figures 17, 18:
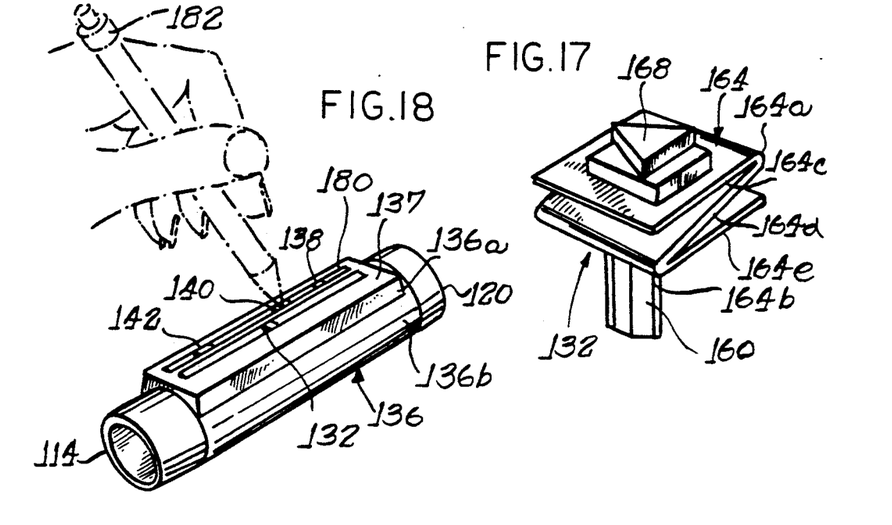
FIG. 17 is an enlarged perspective view of the moveable indicator of the peak flow meter of FIG. 11, showing the Z-shaped friction engaging portion employed to prevent unintentional sliding of the indicator.
FIG. 18 is a perspective view of the peak flow meter of FIG. 11, shown with the color-coded indicators being set by a physician using a writing implement.

With reference to FIGS. 16-18, the sliding indicator 132 and the color-coded indicators 138, 140 and 142 are shown. The sliding indicator 132 includes an inwardly projecting stem 160 which is received within elongated channel 162 in the aluminum body 136 to be engaged by the piston 154 as the piston is advanced to move the sliding indicator 132 to its peak position. As seen in FIG. 17, in this embodiment the sliding indicator also includes a Z-shaped base 164 which resides within the widened portion of T-shaped channel 166, and has an indicating arrow 168 mounted thereto which resides in the narrower portion of the T-shaped channel 166. This compression spring is made of plastic which is thin and flexible and is bent at fold lines 164a and 164b with an upper ply 164c, an oblique ply 164d and a bottom ply 164e. The plies 164a and 164e are compressed by the top and bottom sides 166a and 166b of the channel 166. This compressed spring provides frictional engagement between the sliding indicator 132 and the body 136 so that the sliding indicator 132 remains stationary after being moved to its peak position, despite retraction of the piston 154 and/or tilting of the body 136 of the apparatus following exhalation. This is important to prevent erroneous peak flow readings. The Z-shaped base 164 should, accordingly, be proportioned in relation to the channel 166 and made of a material that provides sufficient frictional engagement to prevent inadvertent sliding of the indicator 132, yet still allow the indicator 132 to slide easily when pushed by the piston 154 during exhalation.

In contrast, the three color-coded indicators 138, 140 and 142 reside and slide within T-shaped channel 180 (FIG. 16) with significantly greater frictional engagement. The illustrated indicators are small block shaped elements which have a wider bottom portion 181 captured in a wider bottom portion 180a of the T-shaped channel 180. The indicator elements may be formed of rubber or other material having a high coefficient of friction and mounted in the channel so that considerable force is needed to reset them. Since the color-coded indicators 138, 140 and 142 are preferably set by a physician and are generally not moved between consecutive uses of the peak flow meter, except when re-set by the physician, the frictional engagement should be sufficient to prevent inadvertent sliding or movement of the indicators during transport or handling, or during tampering by a child. It has been found that these characteristics are provided by making the color-coded indicators 138, 140 and 142 of rubber. To further prevent inadvertent sliding of the color-coded indicators 138, 140 and 142, the indicators may be situated completely below the surface 137 of the body 136. This prevents the color-coded indicators from sliding when brushed against, yet still allows easy movement of the indicators when pushed with an instrument narrow enough to fit within the channel 180. By way of example, FIG. 18 depicts the color-coded indicators being repositioned with use of a common pen 182.

From the foregoing, it will be seen that there has been provided a convenient method for determining human expiratory flow rates, to indicate to the asthmatic what remedial actions to take in case of subtle or gross changes in expiratory flow rate.

What is claimed is:

1. A peak flow meter apparatus for determining lung expiratory flow rate and quantifying deviations from a peak flow rate comprising,
   an elongated body having a passageway into which air is blown and from which air exhausts,
   an air inlet connected to the passageway through which a user blows air,
   a scale mounted on the body,
   an indicator slidable on the body and moveable in relation to the amount and force of air blowing through the inlet and moveable along the scale, and
   zone-indicating means on the elongated body for quantifying each of a plurality of deviations from a pre-selected selected flow rate and cooperating with the slidable indicator to quantify quickly the zone and the respective amount of deviation to which the moveable indicator has been moved to by the force of air.

2. An apparatus in accordance with claim 1 wherein the zone-indicating means comprises a plurality of settable indicators each of a different color and moveable relative to each other to define zones therebetween, each of the colored zones representing a range of deviation from the optimal peak flow rate for the user.

3. An apparatus in accordance with claim 2 including the colored indicators being set adjacent a mark on the scale in accordance with a card which displays compiled data arranged in color-coded zones.

4. An apparatus for determining expiratory flow rate which is a peak flow meter comprising, a hollow, elongated body which has two aperture ends through which air enters and exhausts, one aperture end is an air inlet through which the user blows air, a scale mounted on the body, moveable indicator slidable on the body, moveable in relation to the amount and force of air blowing through body and cooperating with the scale, and adjustable color-coded zone means on the elongated body cooperating with the scale on the body and positionable to indicate the peak expiratory flow rate and zones of percentage of deviation from the peak expiratory flow rate to quantify by a percentage the deviation from the peak expiratory flow rate.

5. An apparatus in accordance with claim 4 wherein the color-coded zone means comprises a slot and a plurality of settable indicators adjustably slidable in the slot and each having different colors to define a different color zone associated with a predetermined percentage from the peak expiratory flow rate.

6. An apparatus in accordance with claim 5 wherein the color-coded zone means comprises settable indicators which correspond to optimal flow rate, 10% below optimal lung flow rate, and 50% below optimal lung flow rate.

7. A method for determining an air expiratory flow rate using a peak flow meter and a zone calculator comprising the steps of:

providing a peak flow meter for expiratory flow rate, determining from a compilation of data related to expiratory flow rate values an expiratory flow rate for a given patient's age and sex and determining percentage deviations from a theoretical peak flow rate for the patient and providing a plurality of zones related to these respective deviations from the expiratory flow rate, setting these zones on the peak flow meter, blowing an indicator on the peak flow meter to one of the zones, reading one of the zones to provide indication relative to a predicted expiratory flow rate and a predetermined range of deviation therefrom.

8. A method in accordance with claim 7 wherein the compilation of data is based on age, sex, and height of the patient.

9. A method in accordance with claim 7 wherein the zones are color-coded and are made up of three colors.

10. A method for determining whether an individual has full or diminished expiratory flow rate comprising:

providing a peak flow meter upon which is mounted a plurality of zone-indicating means, moving the zone-indicating means relative to a scale mounted on the peak flow meter to delineate a plurality of ranges of variation from an optimal expiratory flow rate, blowing air to push an indicator on the peak flow meter to one of the ranges, and reading one of the ranges to provide a quantification of the expiratory flow rate as related to a predetermined range of variation from the optimal expiratory flow rate.

11. A method utilizing a peak flow meter in cooperation with a zone calculator for determining whether an individual has full or diminished expiratory flow rate comprising:

providing a peak flow meter having an elongated, hollow body upon which is mounted a scale in cooperation with three color-coded slidable indicator tabs, setting the three color-coded indicator tabs on the peak flow meter after determining color-zone settings with a zone calculator, which displays a compilation of expiratory flow rate data in relation to the age, sex, and height of the individual, blowing air to push a slidable indicator on the peak flow meter to one of the three color-zones, reading the color-zone in which the slidable indicator comes to rest to identify a predetermined range of variation of the individual's current expiratory flow rate.

12. An apparatus for determining expiratory flow rate which is a peak flow meter comprising, a hollow, elongated body which has two aperture ends through which air enters and exhausts, one aperture end is an air inlet through which the user blows air, a scale mounted on the body, a moveable indicator slidable on the body, moveable in relation to the amount and force of air blowing through the body and cooperating with the scale, and color-coded zone means on the elongated body cooperating with the scale on the body and the moveable indicator to indicate peak expiratory flow rate and predetermined deviations therefrom, the color-coded zone means comprising a slot and a plurality of settable indicators slidable in the slot and having different colors, the slidable indicators being positioned below a top portion of the slot and a tool being needed to engage and push a slidable indicator in the slot.

* * * * *